United States Patent [19]

Pazda et al.

[11] Patent Number: 5,066,918
[45] Date of Patent: Nov. 19, 1991

[54] APPARATUS AND METHOD FOR MEASURING LATERAL CHARGE DISTRIBUTION ON A MOVING WEB

[75] Inventors: Robert J. Pazda, Waterloo; Kenneth L. Clum, Webster; Harrison P. Hood, III, Rochester, all of N.Y.

[73] Assignee: Eastman Kodak Company, Rochester, N.Y.

[21] Appl. No.: 627,174

[22] Filed: Dec. 14, 1990

[51] Int. Cl.⁵ .................. G01N 27/61; G03G 15/00
[52] U.S. Cl. .................. 324/452; 324/454; 355/216
[58] Field of Search .......... 324/452, 454–457, 324/72, 72.5, 663, 690; 355/216, 219, 262, 218

[56] References Cited

U.S. PATENT DOCUMENTS

| | | | |
|---|---|---|---|
| 3,944,354 | 3/1976 | Benwood et al. | 324/455 X |
| 4,780,680 | 10/1988 | Reuter et al. | 324/455 |
| 4,857,853 | 8/1989 | Cook, Jr. | 324/452 X |

OTHER PUBLICATIONS

Ohara et al., Apparatus For Simultaneous Measurements of Static Electricity and Friction of Polymer Films, Journal of Physics E, vol. 9, No. 3, pp. 226–229, 3-1976.
Publication: K. L. Clum and R. J. Pazda—"Segmented Roller: A Device For Measuring Charge Density On A Moving Conducting Web", Journal of Electrostatics, 24 (12-1989), 21-32.

Primary Examiner—Jack B. Harvey
Attorney, Agent, or Firm—Francis H. Boos, Jr.

[57] ABSTRACT

Apparatus for measuring lateral charge distribution on a moving web includes a cylindrical roller having at least a pair of charge measuring segments on the cylinder surface which are electrically isolated from each other and aligned end-to-end in the direction of the axis of rotation of the cylinder. Each of the measurement segments is adapted to be connected to a separate electrometer. The cylinder is mounted on a support to move the cylinder in a direction perpendicular to the longitudinal direction of conveyance of the web over the surface of the cylinder. A measuring device for measuring lateral displacement of the cylinder is used for calculation of the proportion of web area in contact with one segment relative to the total web area in contact with both segments. The proportionate measured charge represents the integral charge on a fraction of the web and by taking periodic measurements as the cylinder is moved laterally across the web, a profile of lateral integral charge distribution is determined. The corresponding profile of lateral charge density distribution is then readily determined by differentiation of the charge distribution profile curve.

5 Claims, 5 Drawing Sheets

APPARATUS AND METHOD FOR MEASURING LATERAL CHARGE DISTRIBUTION ON A MOVING WEB

FIELD OF INVENTION

This invention relates to the field of electrostatic charge measurement and in particular to measurement of electrostatic charge on slightly conductive dielectric webs, such as photographic film strips, moving over grounded metallic conveyor rollers.

BACKGROUND OF INVENTION

It is desirable to understand electrostatic phenomena observed with moving, slightly conductive dielectric webs passing over grounded metallic conveyor rollers. For example, it would be desirable in connection with determining how natural charge limitation occurs in the moving web. To obtain such an understanding, it is important to know how net charge is distributed on the web. If the web has some conductivity so that charge can move on the web, then the distribution will be dynamic, i.e. it will change as the environment through which it passes changes. In such a case, the charge must be analyzed taking into account all the forces which can influence charge movement.

Charge distribution in the lengthwise direction of the web, i.e. in the direction of conveyance of the web over the roller, and apparatus for measuring such lengthwise distribution is described in the article entitled "Segmented Roller: A Device for Measuring Charge Density on a Moving Conducting Web" published in Journal of Electrostatics, Vol. b 24, pages 21-32 (1989). While the apparatus described in that article is capable of measuring lengthwise charge distribution, no capability existed for measuring lateral charge distribution. However, it is important in the context of understanding electrostatic phenomena of moving webs to know the lateral distribution of charge on the web.

It is therefore an object of the present invention to provide apparatus capable of measuring lateral charge distribution on a moving web.

SUMMARY OF INVENTION

In accordance with the invention, therefore, apparatus for measuring lateral charge distribution on an elongated moving web comprises a cylindrical roller rotatable about a central axis of rotation, the outer surface of the roller including a pair of closely adjacent charge measurement segments electrically isolated from each other along a line of separation therebetween, the measurement segments being oriented end-to-end, at the line of separation, in a direction parallel with the axis of rotation of the roller. The measurement segments are adapted during rotation of the roller to periodically engage the moving web in an area of surface contact between the web and at least one of the segments during conveyance of the moving web across a portion of the circumference of the roller. Means are provided for translating the roller in a direction perpendicular to the direction of travel of the web so as to move the line of separation between the segments laterally across the web thereby varying the relative areas of surface contact of each segment with the web. The apparatus of the invention further includes dimensional measurement means for periodically measuring the lateral dimension of the area of surface contact between the web and one of the segments as the roller translates laterally across the web. Charge measurement means coupled to both segments are adapted for periodic measurement of the total charge across the web, whereby lateral integral charge distribution on the web can be determined as a proportion of the web contact surface area of one segment to the total web contact surface area of both segments.

DETAILED DESCRIPTION

Figure 1:
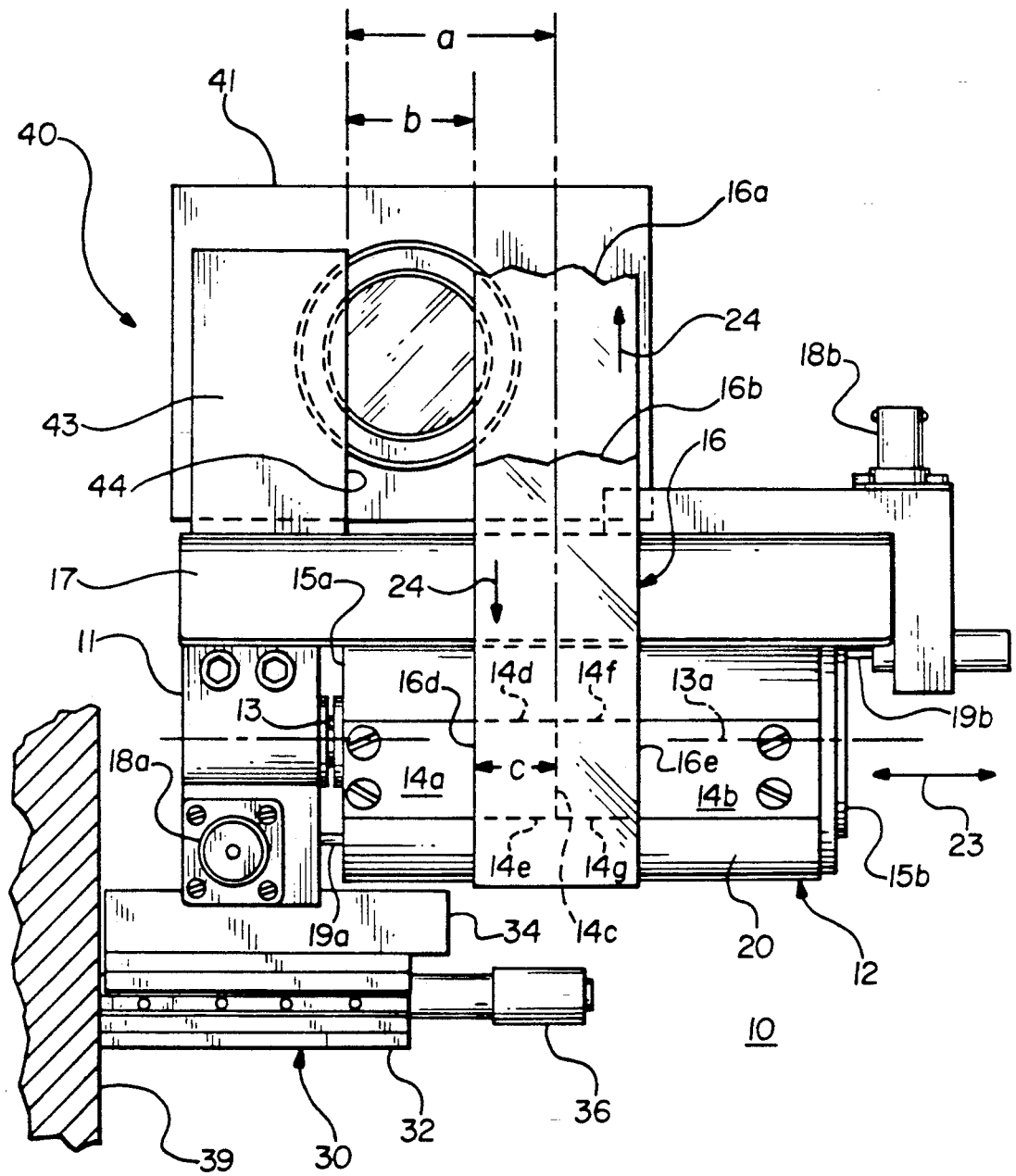
FIG. 1 is a bottom plan view of apparatus for measurement of lateral charge on a moving web constructed in accordance with the present invention.
Figure 2:
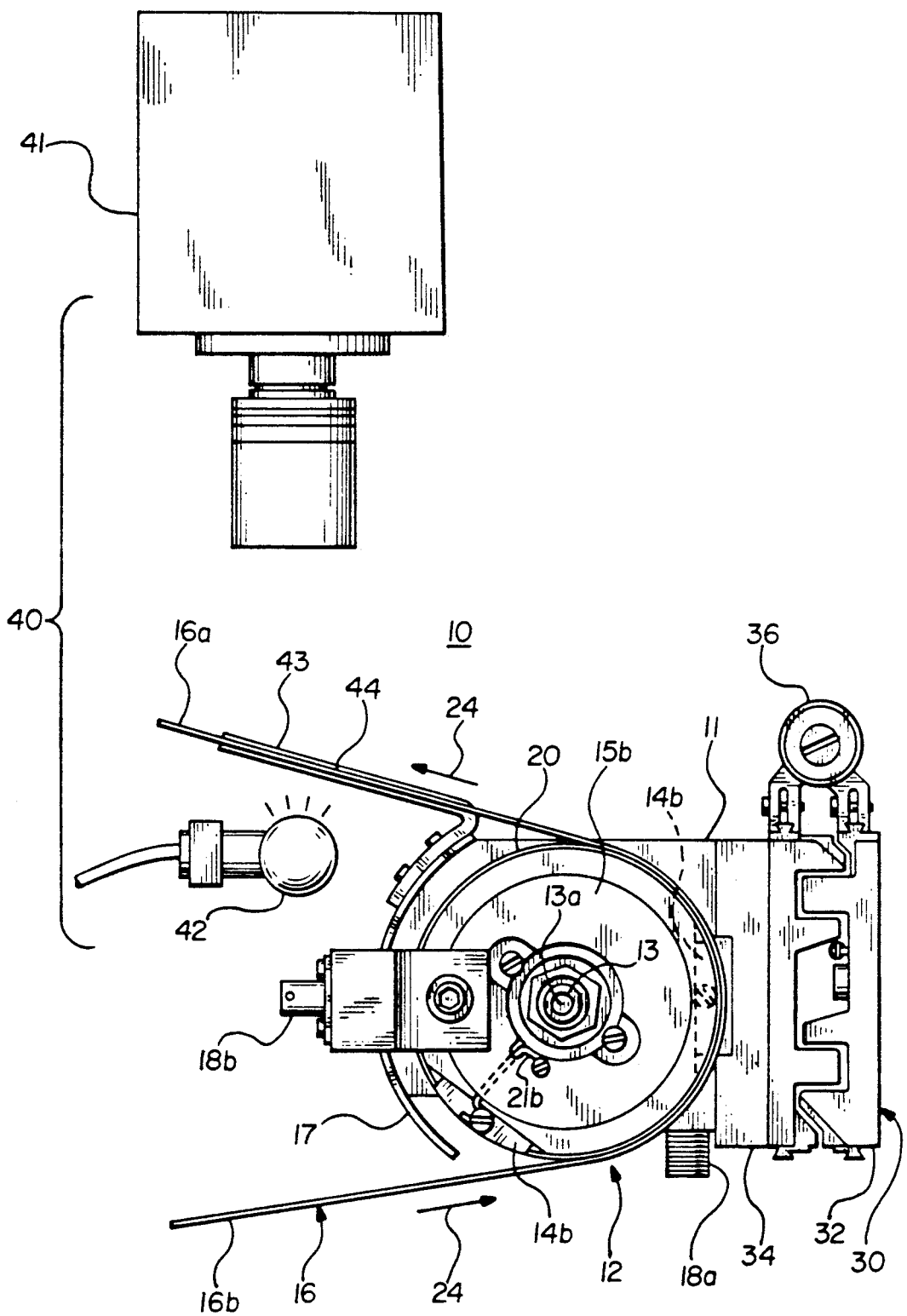
FIG. 2 is a side plan view of the FIG. 1 apparatus.
Figure 3:
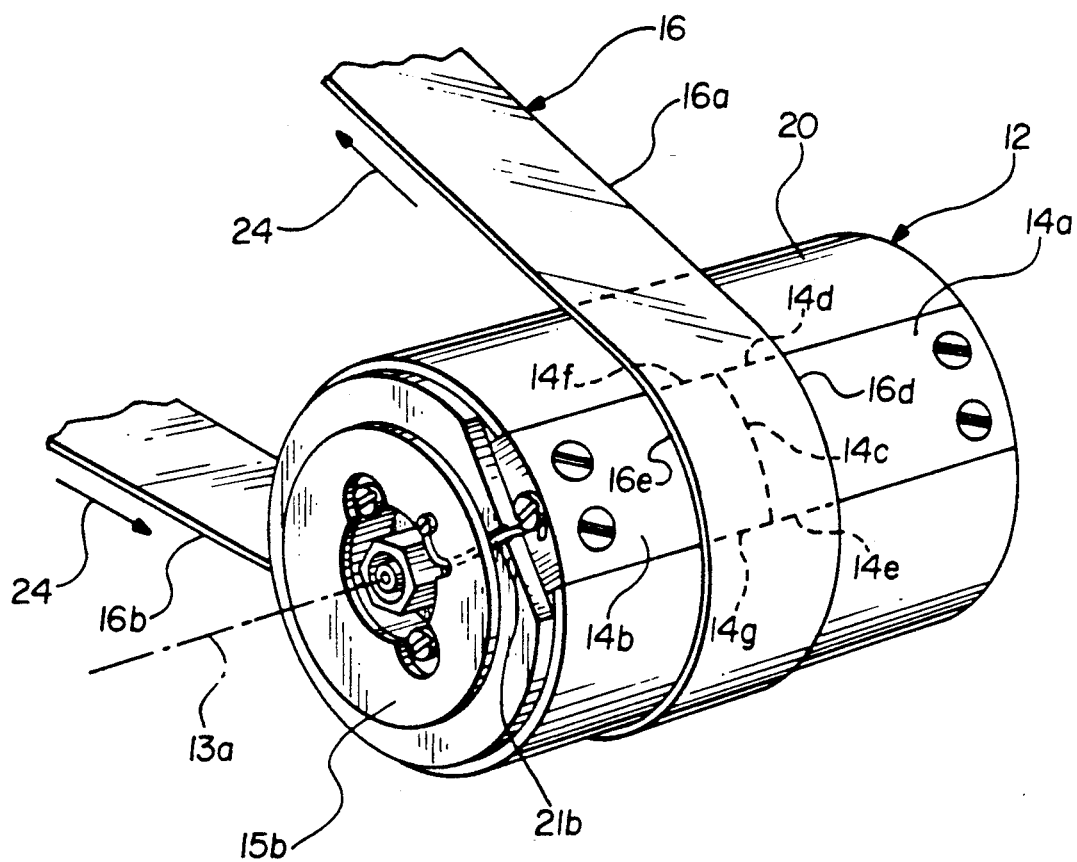
FIG. 3 is a perspective view of a cylindrical roller embodied in the apparatus of FIG. 1.

Referring to FIGS. 1-3 of the drawings, apparatus 10 for measuring lateral charge on a moving web 16, such as an elongated strip of photographic film, is comprised, in part, of a cylindrical roller 12 having an outer surface covered by a semi-cylindrical electrically grounded shell 20 and a pair of charge measurement segments 14a,14b. The core of roller 12 is made of a suitable structural insulating material. Shell 20 and segments 14a, 14b, which may be made of any conductive material such as stainless steel, are mutually electrically isolated, the shell from the segments and the segments from each other. The segments are positioned end-to-end on the roller in a line parallel with the axis of rotation 13a of the roller and are separated by a line of separation 14c preferably midway between the outer ends of the segments. The roller arrangement is such that, in operation, a web 16 is wrapped around a portion of the roller surface and is typically conveyed between supply and take up reels (not shown) and held in tension around roller 12 by means of tension rollers (not shown) preferably mounted remotely on backplane 39. Also, the distance of the web 16 from the backplane 39 is fixed by flanged rollers (not shown) mounted remotely from roller 12. When web 16 is wrapped around the outer surface of roller 12 in this manner and as the roller rotates with conveyance of the web, segments 14a and 14b each periodically contact the web at an area of surface contact. For segment 14a this area is bounded by the side 16d of the web, sides 14d and 14e of segment 14a and the line of separation 14c between the segments. Similarly, the area of surface contact for segment 14b is bounded by the line of separation 14c, segment sides 14f and 14g and side 16e of the web.

Apparatus 10 of the invention further comprises means 30 for translating the roller 12 in a direction perpendicular to the longitudinal direction of travel of web 16 for the purpose of varying the relative area of surface contact between each of the segments 14a,14b and the web 16 in a measured manner. More specifically, means 30 includes a stationary support 32 mounted directly on a backplane wall 39 and further includes a movable support 34 to which roller 12 is rotationally mounted by means of an axle 13 journalled on a support bracket 11 secured to movable support 34.

A semi-cylindrical grounded shield 17 is also mounted on support bracket 11 to provide a shielded environment for periodic measurement of charge on the charge measurement segments 14a,14b independent of the effects of charge on the web as is explained more fully in the Journal of Electrostatics article referred to above, the disclosure of which is incorporated herein by reference. A manually operated micrometer drive knob 36 is coupled by suitable mechanism to support 34 and is used to move support 34 laterally, as indicated by double-ended arrow 23, in either direction parallel to the axis of rotation 13a of roller 12. Alternatively, support 34 could be moved automatically by, for example, a stepper motor driven mechanism. Web 16, partially wrapped around the outer surface of roller 12, is conveyed longitudinally in the direction indicated by arrows 24. For purposes of the invention, the actual direction of longitudinal conveyance of web 16 is not significant, the directional arrows 24 being shown herein merely to aid in visualizing the structure of the apparatus 10.

Apparatus 10 is also comprised of dimensional measurement means 40 for periodically measuring the lateral dimension of the area of surface contact between the web 16 and one of the segments 14a,14b as the roller 12 translates laterally across the web 16. In the particular embodiment of the invention illustrated herein, the dimensional measurement means 40 includes a linear CCD array camera 41, a light source 42 (FIG. 2) and a reference edge 44. Reference edge 44 is formed along one side of a plate 43 shown mounted on shield 17 in such a manner as to lie in the same plane as the section 16a of web 16 which, in the indicated example, is the section of the web as it leaves the roller 12.

Means coupled to each of the charge measurement segments 14a and 14b, and adapted for periodic measurement of the charge on each segment in its respective area of surface contact with the web includes slip rings 15a,15b located at opposite ends of roller 12 and electrically connected by wires 21a and 21b to segments 14a and 14b respectively. The slip rings 15a,15b are, in turn, connected by contact fingers 19a,19b to connectors 18a,18b which are adapted to be connected to externally situated electrometers for measurement of the charge on the respective charge measurement segments 14a,14b.

Figure 4:
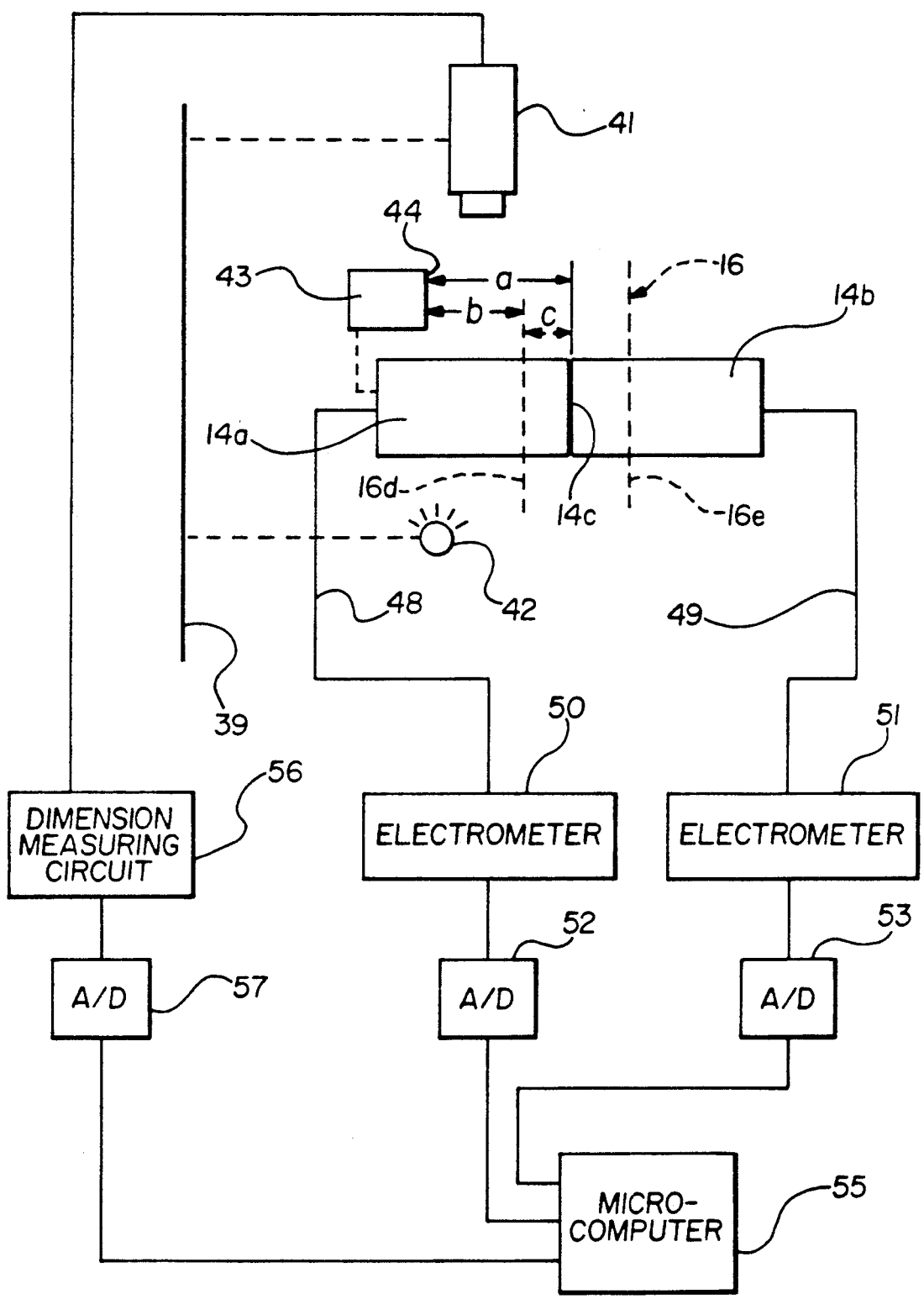
FIG. 4 is a schematic illustration of the measurement apparatus useful in explaining the operation of the invention.

In operation, and with reference to the schematic illustration of FIG. 4, as the web 16 is conveyed over the outer surface of rotating roller 12, the segments 14a and 14b periodically contact the web at the respective areas of surface contact with the web and the web charge on each of these areas is imaged in the corresponding segment. The charge on each of segments 14a and 14b is coupled by lines 48 and 49 to electrometers 50 and 51, respectively. The voltage outputs of the electrometers are converted to digital form by analog-to-digital converters 52 and 53 for application to a microcomputer 55 for data analysis. To determine the lateral charge distribution on the web as it is conveyed over the roller 12, the roller is initially positioned with the line of separation 14c just beyond edge 16d of the web such that, each time the segment 14b contacts the web, all of the charge on the web in the area of surface contact between the web and segment 14b is imaged in the segment 14b. Then as translation means 30 moves the roller 12 incrementally away from the ground plane wall 39 and laterally across the web, the line of separation 14c moves underneath the web causing a portion of the web charge to be imaged in segment 14a. Each time the segments contact the web, the charge, $q_a$, imaged in segment 14a and the charge, $q_b$, imaged in segment 14b are measured and the measurements are stored in the memory of microcomputer 55. The fraction, $Q_a$, of the total charge on segment 14a is then equal to the value $q_a/(q_a+q_b)$.

In order to determine the lateral charge distribution on the web, it is necessary to know the area of the web that is in contact with the segments each time the charge measurement is made. Consequently, simultaneous with each charge measurement, the exposure of light source 42 between reference edge 44 and edge 16d of the web is sensed by the linear CCD array camera 41 and converted by circuit 56 to a voltage proportional to the linear dimension "b". This voltage is then converted to digital form by A/D converter 57 and stored in memory in microcomputer 55. The fixed distance "a" between the reference edge 44 and the line of separation 14c is previously stored in the microcomputer 55 as a reference. With this input information, the microcomputer can then compute the unknown distance "c" from the relation:

$$c=(a-b)$$

Knowing the lateral dimension "c", the microcomputer is then able to calculate, $F_a$, the fraction of the total web width which is in contact with segment 14a.

Figure 5:
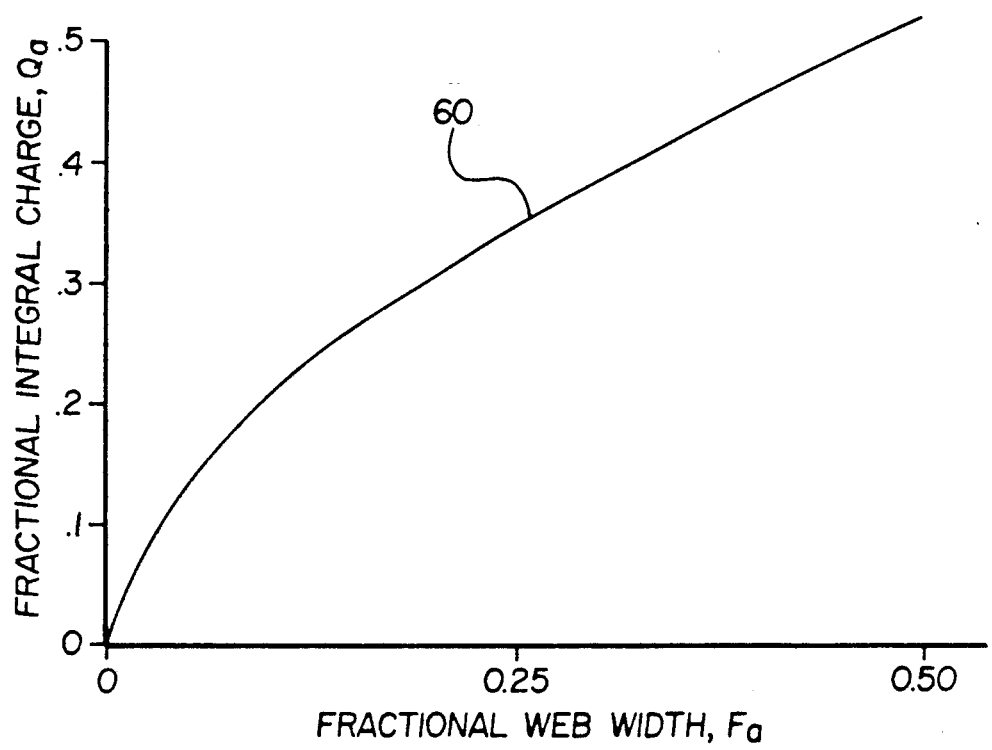
FIG. 5 is a graph of web charge profiles useful in explaining the invention.

It will be appreciated that the direct measurement of charge as just described provides the integral charge on the surface area of contact between the web 16 and the measurement segment 14a. By taking this measurement incrementally across the lateral dimension of the web, a profile of the fractional integral charge, $Q_a$, on the web surface is determined as graphically illustrated by curve 60 of FIG. 5. From this profile, microcomputer 55 can be programmed to differentiate the charge measurements to convert to the incremental charge density at each point along the lateral dimension of the web.

The invention has been described in detail with particular reference to a presently preferred embodiment, but it will be understood that variations and modifications can be effected within the spirit and scope of the invention. For example, although only two charge measurement segments are shown in the illustrated embodiment, it will be readily appreciated that the segments could be subdivided into three or more segments each of which would be coupled to respective slip rings at the ends of the roller.

What is claimed is:

1. Apparatus for measuring lateral charge distribution on an elongated moving web comprising:
    a cylindrical roller rotatable about a central axis of rotation, the outer surface of the roller including a plurality of closely adjacent charge measurement segments electrically isolated from each other along a line of separation therebetween, the measurement segments being oriented end-to-end, at the line of separation, in a direction parallel with the axis of rotation of the roller, the measurement segments being adapted during rotation of the roller to periodically engage the moving web in an area of surface contact between the web and at least one of the measurement segments during conveyance of the moving web across a portion of the circumference of the roller;

means for translating the roller in a direction perpendicular to the direction of travel of the web so as to move the line of separation between the segments laterally across the web thereby varying the relative areas of surface contact of each segment with the web;

dimensional measurement means for periodically measuring the lateral dimension of the area of surface contact between the web and one of the segments as the roller translates laterally across the web;

and means coupled to both segments adapted for periodic measurement of the charge separately on each segment in the respective area of surface contact between each segment and the web, whereby lateral integral charge distribution on the web can be determined as a function of the web contact surface area of one segment to the total web contact surface area of both segments.

2. Apparatus according to claim 1, in which said dimensional measurement means includes reference means movable with translation of the roller at a predetermined spacing from the line of separation between the segments.

3. Apparatus according to claim 1, in which said dimensional measurement means includes a reference edge parallel with an edge of the web adjacent the roller, said reference edge being movable with translation of the roller at a predetermined spacing from the line of separation between the measurement segments.

4. Apparatus according to claim 3 in which there is further included linear array camera means focussed on said reference edge and said web edge for detection of the variable spacing between the reference edge and web edge as the roller is translated laterally across the web.

5. A method of measuring lateral charge distribution on a moving web comprising:

providing a cylindrical roller rotatable about a central axis of rotation and having an outer surface provided with first and second charge measurement segments electrically isolated from each other along a line of separation therebetween, the measurement segments being oriented end-to-end, at the line of separation, in a direction parallel with the axis of rotation of the roller, such that the measurement segments, during rotation of the roller, periodically engage the moving web in an area of surface contact between the web and at least one of the measurement segments during conveyance of the moving web across a portion of the circumference of the roller;

conveying the moving web around a portion of the roller circumference to form said area of surface contact between the web and the roller and to bring at least one of the charge measurement segments periodically into contact with the web within the area of surface contact as the roller rotates;

translating the roller in a direction perpendicular to the direction of conveyance of the web so as to move the line of separation between the segments laterally across the web thereby varying the relative area of surface contact between the web and each of the segments;

periodically measuring the lateral dimension of the surface area of contact between the web and one of the segments as the roller moves across the web;

periodically measuring the total charge on the charge measurement segments as the web is conveyed across the roller;

and periodically determining the lateral integral charge distribution on the web by calculation from the lateral dimension measurement and the proportion of the total measured charge which is imaged in said one segment.

* * * * *